United States Patent
Barbut

(12) 
(10) Patent No.: US 6,623,471 B1
(45) Date of Patent: Sep. 23, 2003

(54) DEVICES AND METHODS FOR PREVENTING DISTAL EMBOLIZATION FROM THE INTERNAL CAROTID ARTERY USING FLOW REVERSAL BY PARTIAL OCCLUSION OF THE EXTERNAL CAROTID ARTERY

(75) Inventor: Denise R. Barbut, New York, NY (US)

(73) Assignee: CoAxia, Inc., Maple Grove, MI (US)

( * ) Notice: Subject to any disclaimer, the term of this patent is extended or adjusted under 35 U.S.C. 154(b) by 4 days.

(21) Appl. No.: 09/687,150

(22) Filed: Oct. 12, 2000

Related U.S. Application Data

(63) Continuation of application No. 09/287,252, filed on Apr. 7, 1999, now Pat. No. 6,146,370.

(51) Int. Cl.⁷ .............................................. A61M 31/00
(52) U.S. Cl. ..................... 604/509; 604/500; 604/96.01; 604/915
(58) Field of Search ................... 604/509, 500, 604/101.01, 508, 101.04, 101.05, 103.07, 532, 96.01, 915; 606/191, 194, 195, 200; 128/898

(56) References Cited

U.S. PATENT DOCUMENTS

| | | | |
|---|---|---|---|
| 4,921,478 A | | 5/1990 | Solano et al. |
| 5,312,344 A | * | 5/1994 | Grinfeld et al. ............ 604/101 |
| 5,423,742 A | | 6/1995 | Theron |
| 5,599,307 A | | 2/1997 | Bacher et al. |
| 5,765,568 A | | 6/1998 | Sweezer, Jr. et al. |
| 5,769,812 A | | 6/1998 | Stevens et al. |
| 5,833,645 A | | 11/1998 | Lieber et al. |
| 5,833,650 A | * | 11/1998 | Imran ..................... 604/53 |
| 5,938,645 A | | 8/1999 | Gordon |
| 6,206,868 B1 | | 3/2001 | Parodi |

FOREIGN PATENT DOCUMENTS

WO   WO 99/45835   * 9/1999

OTHER PUBLICATIONS

Theron, J. et al., "New Triple Coaxial Catheter System for Carotid Angioplasty with Cerebral Protection," *American Journal of Neuroradiology*, Sep./Oct. 1990, pp. 869–874, vol. 11, American Society of Neuroradiology, USA.

* cited by examiner

*Primary Examiner*—Brian L. Casler
*Assistant Examiner*—Jennifer Maynard
(74) *Attorney, Agent, or Firm*—O'Melveny & Myers LLP

(57) ABSTRACT

The invention provides a medical device having a catheter, an expandable occluding member and a constricting member. The catheter has a lumen communicating with a port at its distal end. The lumen and port are adapted for introduction of therapeutic or diagnostic devices, including an angioplasty/stent catheter, an atherectomy catheter, and a blood filter, into the carotid artery. The occluder is mounted proximal to the port of the catheter, and the constrictor is mounted distal to the port. Manometers may be mounted distal to the occluder and/or the constrictor for measuring pressure proximal and distal to the constrictor. A pump, operably associated with a shunt mounted through a second occluder, may be used instead of the constrictor to facilitate passage of blood through the second occluder. Methods of using the devices for preventing distal embolization during carotid procedures by reversing blood flow in the internal carotid artery toward the external carotid artery are disclosed.

11 Claims, 11 Drawing Sheets

DEVICES AND METHODS FOR PREVENTING DISTAL EMBOLIZATION FROM THE INTERNAL CAROTID ARTERY USING FLOW REVERSAL BY PARTIAL OCCLUSION OF THE EXTERNAL CAROTID ARTERY

This is a continuation of U.S. application Ser. No. 09/287,252, filed Apr. 7, 1999, now U.S. Pat. No. 6,146,370, which is expressly incorporated herein by reference in its entirety.

FIELD OF THE INVENTION

The present invention relates generally to devices and methods useful in treating patients with stroke or occlusive cerebrovascular disease. More specifically, the invention provides an extracranial device capable of reversing flow down an internal carotid artery, and into the external carotid artery during an invasive carotid procedure, thereby avoiding distal embolization of vascular debris. Various diagnostic or therapeutic instruments, including an atherectomy catheter, a filter, and/or an angioplasty/stent catheter, can be introduced through the device for treating the carotid occlusion. The invention may also be useful to reverse flow during a stroke.

BACKGROUND OF THE INVENTION

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Outcome following stroke is influenced by a number of factors, the most important being the nature and severity of the resulting neurologic deficit. Overall, less than 80% of patients with stroke survive for at least 1 month, and approximately 35% have been cited for the 10-year survival rates. Of patients who survive the acute period, up to 75% regain independent function, while approximately 15% require institutional care.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are hemispheric ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. The internal carotid artery, commonly affected by atherosclerosis causing symptomatic occlusion in the arterial lumen, is often responsible for hemispheric ischemic stroke and generating thromboembolic material downstream to the distal cerebral vessels. Treatment of the occluded carotid artery in patients with stroke and TIA or for stroke prevention in patients with asymptomatic flow limiting carotid stenosis undergoing major cardiothoracic surgeries includes performing angioplasty, stent placement, or atherectomy on the occluded carotid artery. Unfortunately, placing instrumentation within a diseased carotid artery is associated with increased risk of ischemic stroke, since manipulation of an atheromatous plaque in the arterial wall often causes emboli to dislodge distally in the narrow cerebral arteries.

Current methods of preventing distal embolization from carotid instrumentation include insertion of a blood filter distal to the occlusion and suctioning embolic debris during the procedures. Disadvantages associated with the conventional methods are that (1) inserting the filter through the atheromatous lesion is associated with increased risk of distal embolization, (2) using suction to reverse the flow in the internal carotid artery may increase a patient's blood loss if the suctioned blood is discarded, and (3) systemic anticoagulation and pumping may be required to recycle the suctioned blood back into the arterial or venous system, and such anticoagulation is associated with increased risk of hemorrhage.

New devices and methods are thus needed in patients undergoing carotid procedures for definitive or prophylactic treatment of carotid plaque, which minimize the risk of distal embolization and prevent ischemic stroke.

SUMMARY OF THE INVENTION

The invention provides devices and methods for preventing ischemic stroke in patients undergoing invasive carotid procedures, including angioplasty, stent placement, and/or filter insertion, by reversing blood flow down an internal carotid artery and up the ipsilateral external carotid artery. In this way, embolic debris generated as a result of placing instrumentation within a diseased carotid artery is diverted to the external carotid artery, thereby preventing stroke by minimizing distal embolization to the narrow cerebral vessels. The devices and methods are also useful to remove an embolus and improve flow (by reversing collateral blood flow across the circle of Willis) in patients with acute stroke.

One embodiment of the medical device comprises a catheter and two expandable occlusion members. The catheter has a lumen communicating with a proximal end and a distal port at its distal end. The lumen is adapted for insertion of a therapeutic instrument, such as an angioplasty, stent, and/or blood filter catheter. An occluder is mounted near the distal end of the catheter proximal to the port. A constrictor is mounted near the distal end of the catheter distal to the port. The expandable occluder and constrictor may be elastomeric balloons. Each of the balloon occluder and constrictor communicates with an inflation lumen and an inflation port at the proximal end of the catheter. The constrictor may be a toroidal balloon or a device of any other appropriate shape, so that it allows passage of blood. The constrictor is mounted on a second member which is slidably insertable through the catheter, and passes beyond the occluder. In this way, the second member and the constrictor are moveable longitudinally relative to the first occluder. In other embodiments, the constrictor may consist of a balloon having more than one opening at its center for the passage of blood, or may consist of more than one expandable balloons allowing passage of blood through the gap between the arterial wall and the expanded balloons.

In another embodiment, a manometer is mounted distal to the occluder for monitoring blood pressure between the occluder and the constrictor. A second manometer may be mounted distal to the constrictor for monitoring blood pressure distal to the constrictor. The proximal end of the catheter may include a hemostatic valve.

In still another embodiment, the catheter includes a second lumen communicating with a proximal end and an infusion port at its distal end. The port is located distal to the distal port of the catheter. The second lumen and its port are adapted for delivering a pharmaceutical agent to the carotid artery, including an angiographic dye.

In still another embodiment, a second or distal occluder includes a shunt for the passage of blood therethrough. The shunt comprises a tube having a lumen communicating with a proximal end and a distal end. A pump is operably associated with the shunt to facilitate delivery of blood from the proximal end of the shunt to the distal end of the shunt, thereby moving blood through the second occluder. The pump may be a helical screw pump included in the lumen of the shunt. The pump may be heparin coated to prevent thrombi formation.

The invention provides methods for reversing flow in a carotid artery which branches into first and second distal segments, where the first distal segment has an atheromatous lesion. More specifically, the methods are useful in reversing flow down an internal carotid artery (ICA) and up the external carotid artery (ECA), where both the ICA and the ECA are distal segments of the common carotid artery (CCA). In a first method, using the devices described above, the distal end of the catheter is inserted into the CCA. The catheter can be inserted over a guide wire through an incision on a peripheral artery, including the femoral artery, the subclavian artery, the brachiocephalic artery, or the common carotid artery. The catheter is positioned to locate the occluder within the CCA, and then to locate the constrictor within the ECA by operating the second member and the constrictor through the catheter. Preferably, the occluder is expanded to completely or partially occlude the CCA. At a critically low CCA pressure, blood flow in the ICA is reversed to pass over the atheromatous lesion and into the ECA. The flow reversal can be verified fluoroscopically with dye. If flow reversal fails to occur or if augmentation of flow reversal is desired, the ECA constrictor is expanded, further reducing the pressure in the ECA to facilitate reversal of flow down the ICA and into the ECA. In an alternative yet less preferred embodiment, the constrictor is expanded to occlude the ECA. The occluder is then partially or completely expanded, causing a decline in the CCA pressure. At a critically low CCA pressure, blood flow in the ICA is reversed to pass over the atheromatous lesion and into the ECA.

After blood reversal is confirmed, procedures on either the ICA or bifurcation of the CCA can be performed by advancing a therapeutic or diagnostic instrument through the lumen and port of the catheter distal to the occluder. An atherectomy catheter, for example, can be introduced to remove the atheroma in the ICA without fear of distal embolization.

In another method, using the device having a second occluder including a shunt for the passage of blood therethrough, the catheter is inserted in the carotid artery, with the second occluder located in the ECA and the first occluder located in the CCA. Preferably, the first occluder is expanded to occlude the CCA followed by expansion of the second occluder to occlude the ECA. Alternatively, the second occluder is expanded to occlude the ECA followed by expansion of the first occluder to occlude the CCA. A pump, traversing the ECA occluder, is activated to facilitate blood reversal from the ICA toward the ECA by moving blood through a shunt included in the second occluder. The flow rate across the second occluder in the ECA can be variably controlled by the pump.

It will be understood that there are several advantages in using the devices and methods disclosed herein for prevention of distal embolization during use of instrumentation in the carotid artery. For example, the devices (1) abolish the need for suction distal to the CCA occluder, thereby minimizing blood loss, (2) eliminate the need for systemic anticoagulation, pumping, and a second arterial or venous stick, all of which are required where suction is employed, (3) can be used to introduce a variety of diagnostic or therapeutic instrument to the carotid artery, (4) can be used in any procedures which require instrumentation within the carotid artery, (5) can be used for definitive treatment of acute or subacute ischemic stroke, (6) can be used in the angiogram or fluoroscopy suite available in most hospitals, and (7) require only one incision site for entry.

DETAILED DESCRIPTION

The cerebral circulation is regulated in such a way that a constant total cerebral blood flow (CBF) is generally maintained under varying conditions. For example, a reduction in flow to one part of the brain, such as in stroke, may be compensated by an increase in flow to another part, so that CBF to any one region of the brain remains unchanged. More importantly, when one part of the brain becomes ischemic due to a vascular occlusion, the brain compensates by increasing blood flow to the ischemic area through its collateral circulation via the Circle of Willis.

Figure 1:
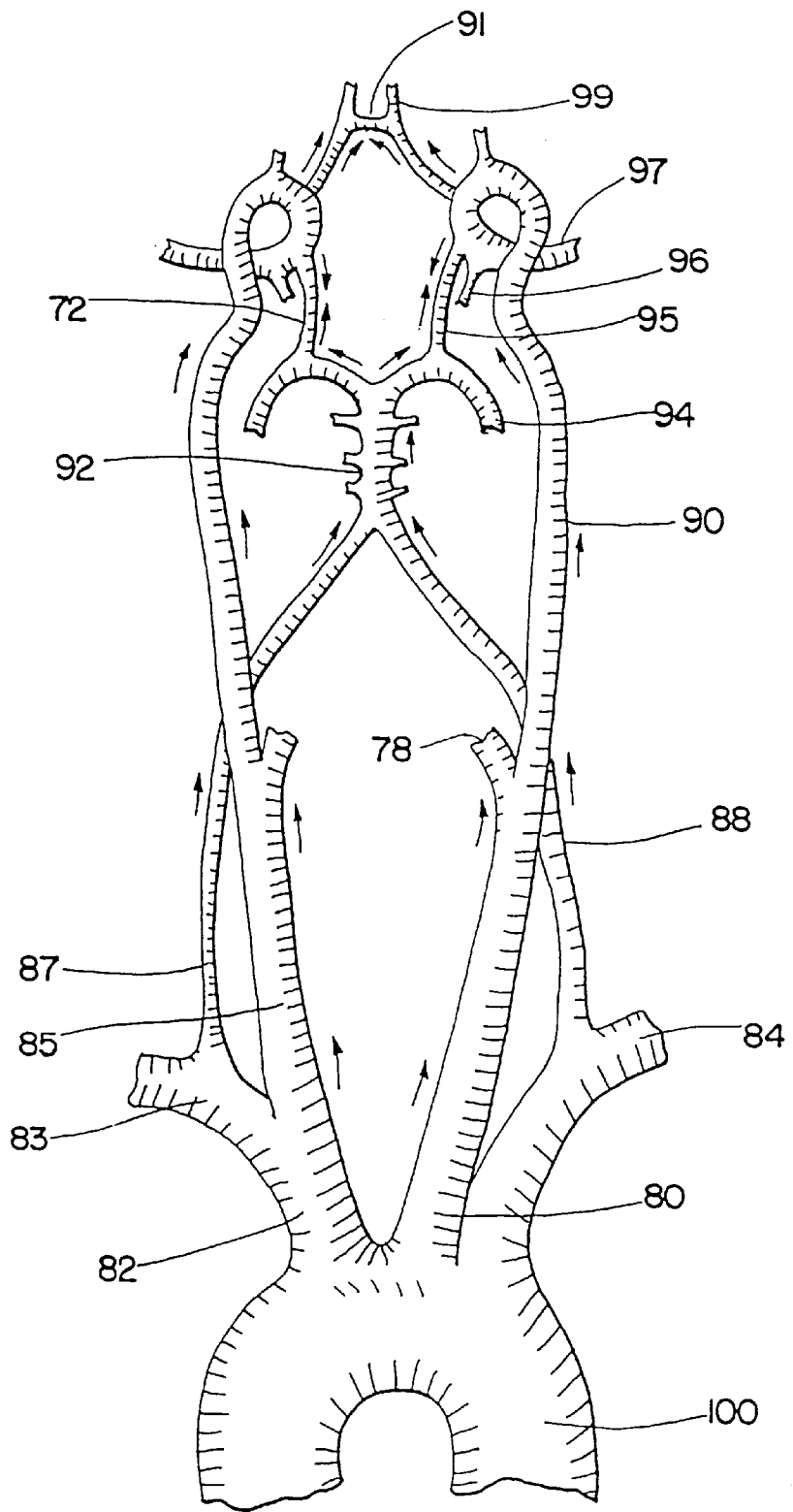
FIG. 1 depicts normal cerebral circulation in the Circle of Willis.

FIG. 1 depicts a normal cerebral circulation and formation of Circle of Willis. Aorta 100 gives rise to right brachiocephalic trunk 82, left common carotid artery (CCA) 80, and left subclavian artery 84. The brachiocephalic artery further branches into right common carotid artery 85 and right subdlavian artery 83. The left CCA gives rise to left internal carotid artery (ICA) 90 which becomes left middle cerebral artery (MCA) 97 and left anterior cerebral artery (ACA) 99. Anteriorly, the Circle of Willis is formed by the internal carotid arteries, the anterior cerebral arteries, and anterior communicating artery 91 which connects the two ACAs. The right and left ICA also send right posterior communicating artery 72 and left posterior communicating artery 95 to connect respectively with right posterior cerebral artery (PCA) 74 and left PCA 94. The two posterior communicating arteries and PCAs, and the origin of the posterior cerebral from basilar artery 92 complete the circle posteriorly. The left CCA also gives rise to external carotid artery (ECA) 78, which branches extensively to supply most of the structures of the head except the brain and the contents of the orbit. The ECA also helps supply structures in the neck.

Figure 2:
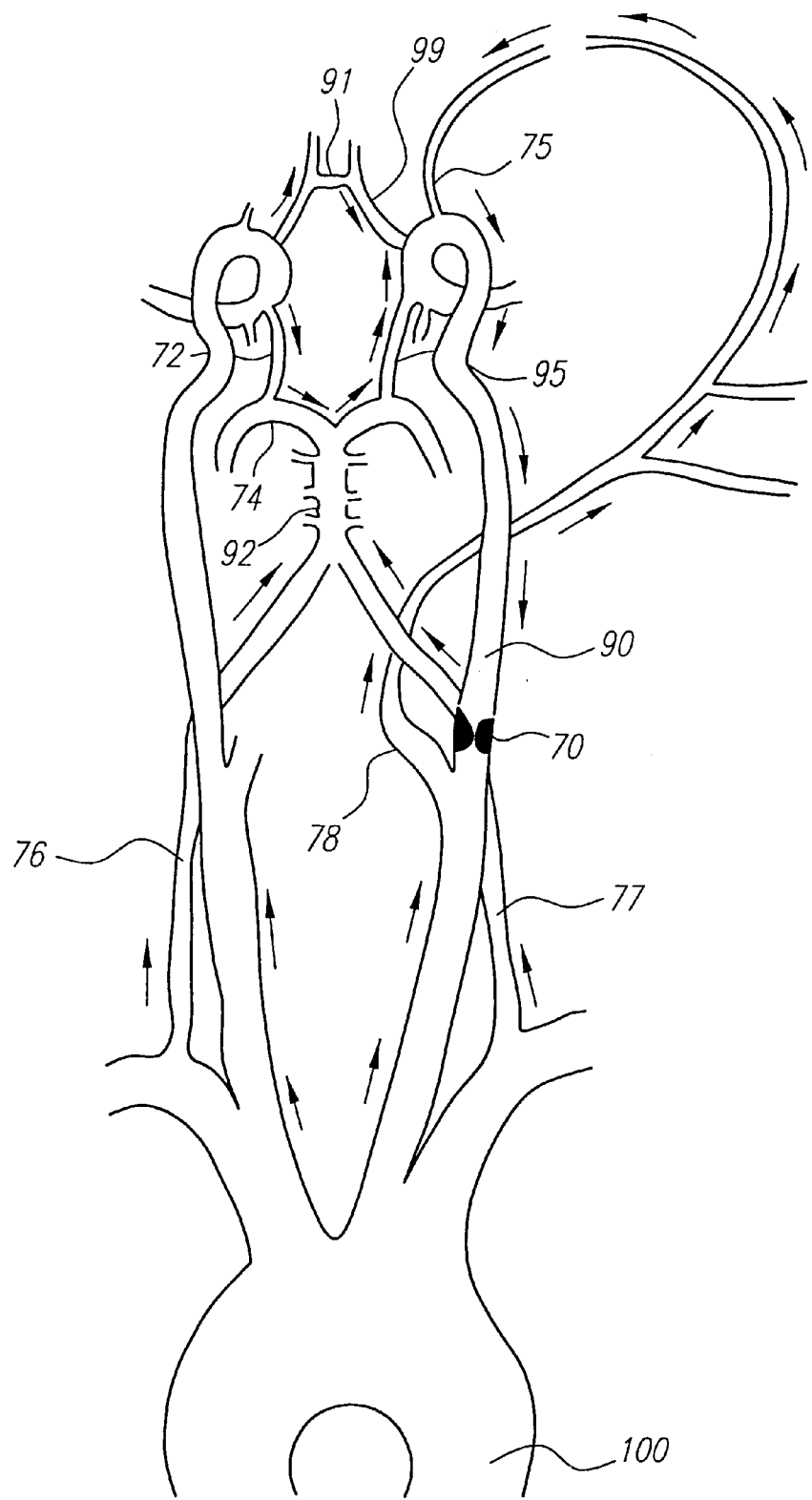
FIG. 2 depicts a reversed circulation in the Circle of Willis to compensate for an occlusion in the left internal carotid artery.

When occluding lesion 70 occurs acutely, for example, in left internal carotid artery 90, as depicted in FIG. 2, blood flow in the right cerebral arteries, left external carotid artery 78, right vertebral artery 76, and left vertebral artery 77 increases, resulting in a directional change of flow through the Circle of Willis to compensate for the sudden decrease of blood flow in the left internal carotid artery. Specifically, blood flow reverses in right posterior communicating artery 72, right PCA 74, and left posterior communicating artery 95. Anterior communicating artery 91 opens, reversing flow in left ACA 99, and flow increases in the left external carotid artery, reversing flow along left ophthalmic artery 75, all of which contribute to flow in left ICA 90 distal to the occluding lesion.

Figure 3:
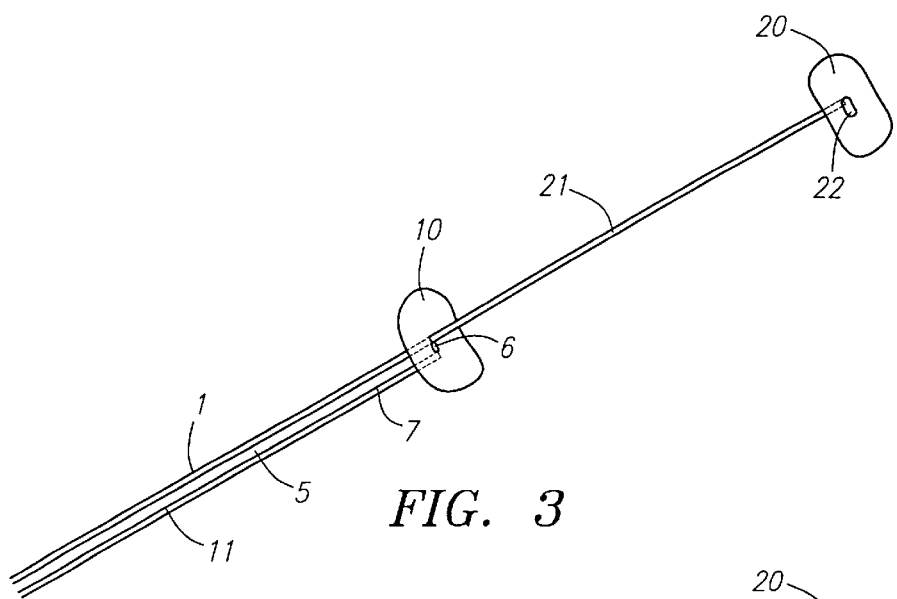
FIG. 3 depicts a distal region of an embodiment of the medical device for prevention of acute stroke during use of instrumentation in a carotid artery.

FIGS. 3 depicts one embodiment of the device for preventing distal embolization during carotid instrumentation. The device comprises catheter 1 and balloon occluder 10 and constrictor 20. The catheter has lumen 5 communicating with a proximal end and port 6 at distal end 7. The lumen and port are adapted for introduction of therapeutic or diagnostic instruments, e.g., atherectomy catheter, angioplasty catheter, stent, and filter, to a carotid artery. Balloon occluder 10, communicating with inflation lumen 11, is mounted on the distal end of the catheter proximal to port 6. Balloon constrictor 20, communicating with inflation lumen 21, is mounted distal to port 6 and first occluder 10. The constrictor has central opening 22 which allows passage of blood. Inflation lumen 21 is an elongate member which, in certain embodiments, is slidably inserted through catheter 1, and is moveable longitudinally relative to catheter 1 and occluder 10.

Figure 4:
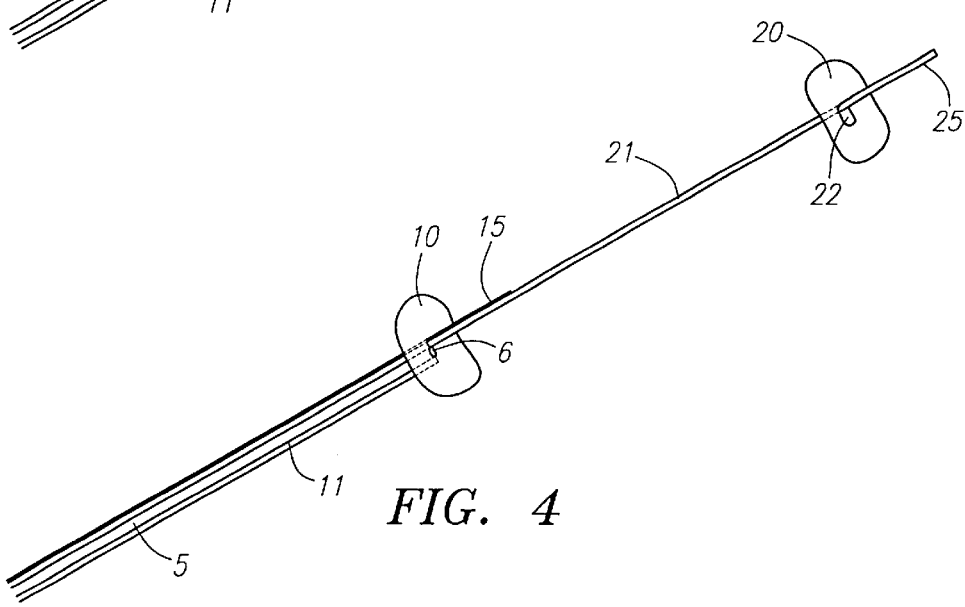
FIG. 4 depicts a distal region of another embodiment of the device having two manometers.

FIG. 4 depicts another embodiment of the device having two manometers. Manometer 15 is mounted distal to occluder 10 for measuring blood pressure between the occluder and the constrictor. Manometer 25 is mounted distal to constrictor 20 for measuring blood pressure downstream from constrictor 20.

Figure 5:
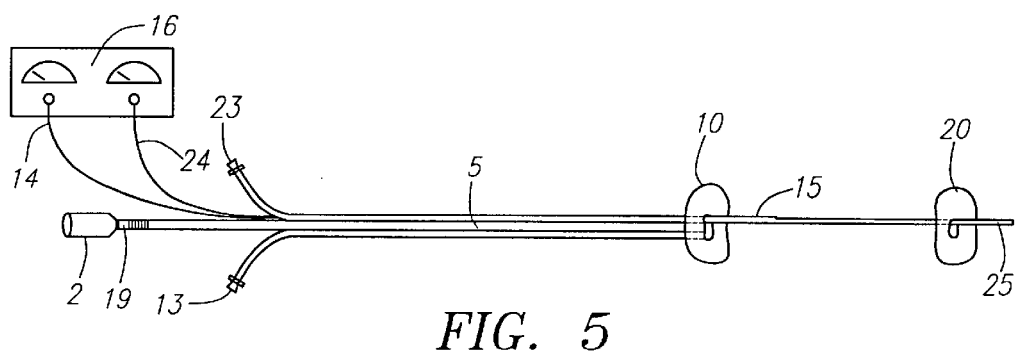
FIG. 5 depicts the device of FIG. 4 including a hemostatic valve at its proximal end.

In FIG. 5, proximal ends 14 and 24 of respective manometers 15 and 25 are connected to pressure monitor 16 for measuring blood pressure proximal and distal the constrictor. Inflation ports 13 and 23 communicate, respectively, with inflation lumens 11 and 21 for expanding balloon occluder 10 and constrictor 20. Lumen 5 of the catheter communicates with proximal end 2 which includes hemostatic valve 19.

Figure 6A:
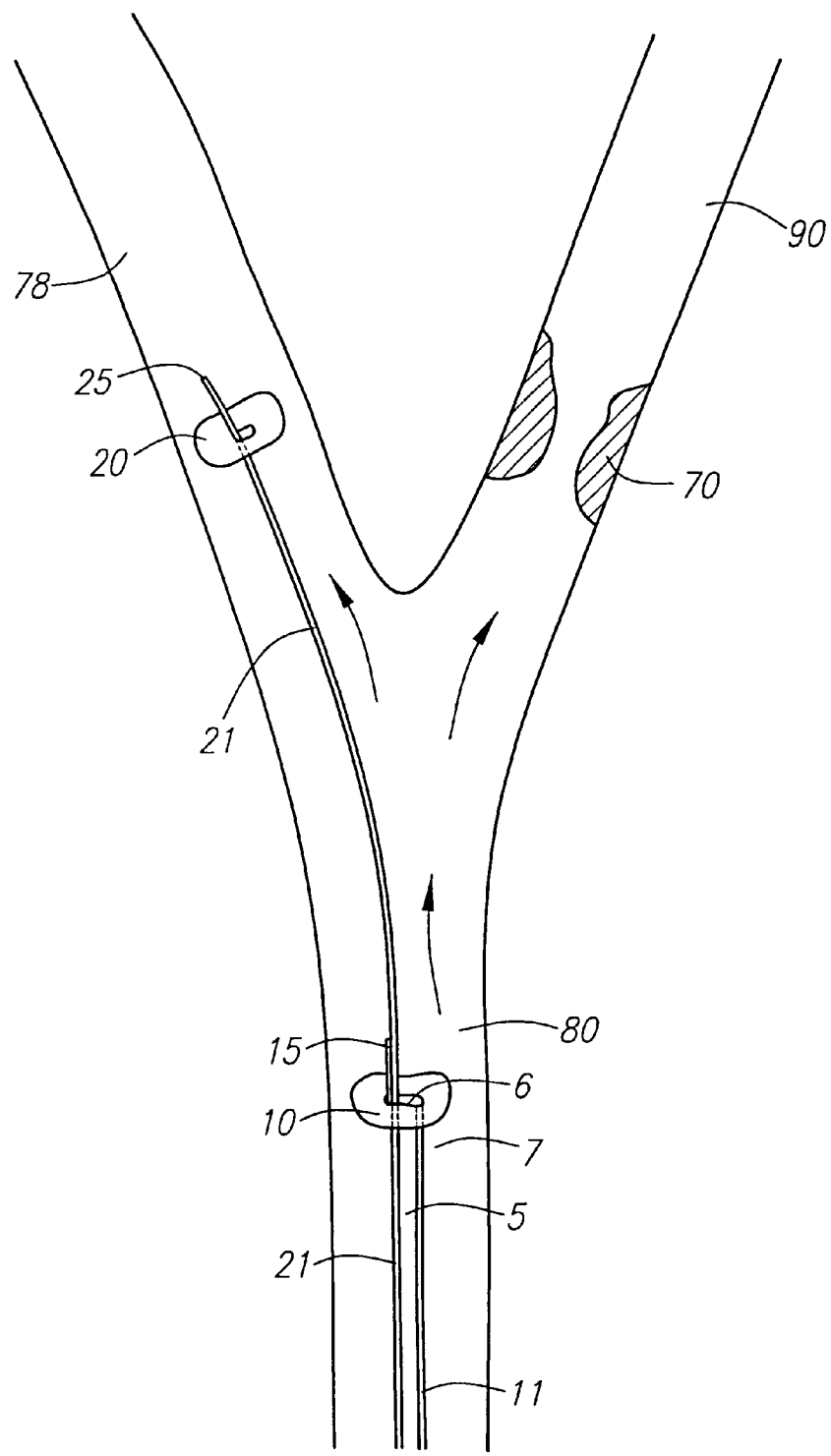
FIG. 6A depicts the device of FIG. 5 inserted in the carotid arteries.

In using the device of FIG. 5, a percutaneous incision is made on the common carotid artery or a peripheral artery, such as the femoral artery. A guide wire is inserted through the incision into the CCA in an antegrade direction. Distal end 7 of the catheter is inserted over the guide wire in the CCA, so that occluder 10 is positioned in CCA 80 and constrictor 20 is positioned in ECA 88 as shown in FIG. 6A. The guide wire is then removed from the catheter. The separation between occluder 10 and constrictor 20 is adjusted to ensure proper placement in the respective arteries.

Figure 6B:
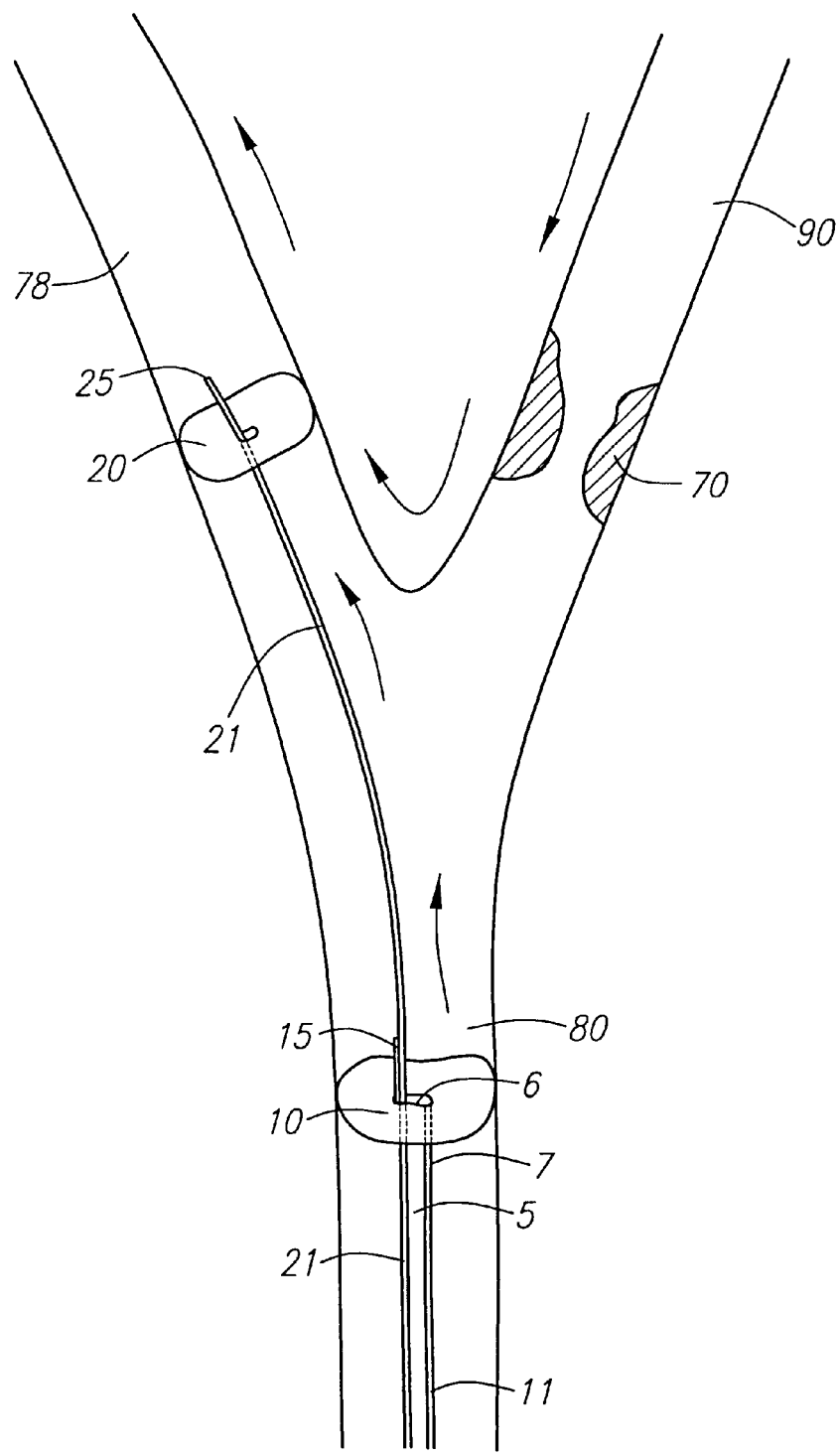
FIG. 6B depicts the device of FIG. 5 inserted in the carotid arteries with expanded occluders causing reversal of blood flow.

Preferably, occluder 10 is slowly expanded through inflation lumen 11 to constrict CCA 80, causing progressive decline in the ECA pressure as shown in FIG. 6B. The pressure in the ECA distal to the constrictor and the pressure in the CCA distal to the occluder can be measured, respectively, by manometers 25 and 15. At a critically low pressure in the distal CCA, blood flow in ICA 90 reverses to pass over atheromatous lesion 70 and into the ECA. The reversal of blood flow down the ICA and up the ECA can be verified fluoroscopically with dye. If flow reversal dose not occur due to insufficient blood flow from contralateral circulation to the ICA, i.e., insufficient pressure gradient between the ICA and the ECA, constrictor 20 is expanded through inflation lumen 21 to further reduce the ECA pressure to create a favorable pressure gradient between the ICA and the ECA to reverse blood flow into the ECA.

Figure 7A:
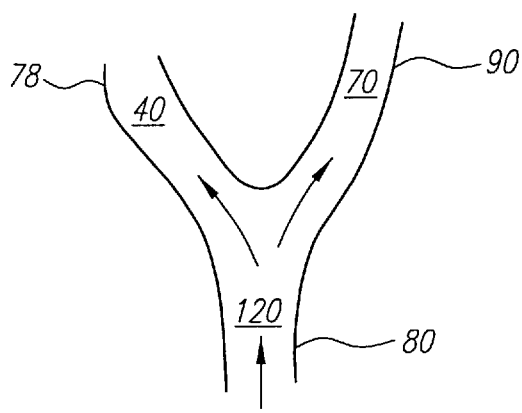
FIG. 7A depicts flow and pressure in the CCA, ECA, and ICA in a patient without carotid stenosis.
Figure 7B:
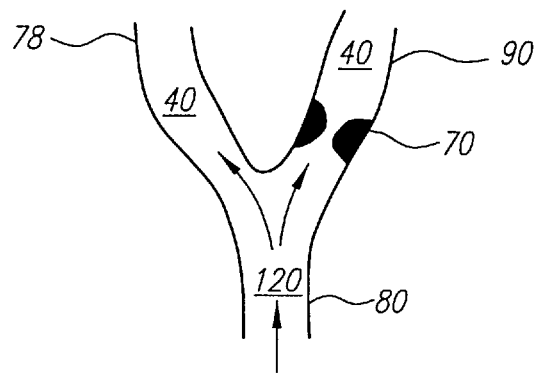
FIG. 7B depicts pressure in the CCA, ECA, and ICA with a stenosis in the ICA.
Figure 7C:
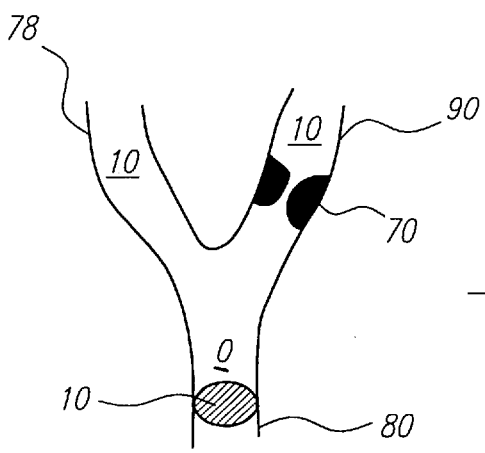
FIG. 7C depicts pressure change in the CCA, ECA, and ICA with complete occlusion of the CCA by an occluder.
Figure 7D:
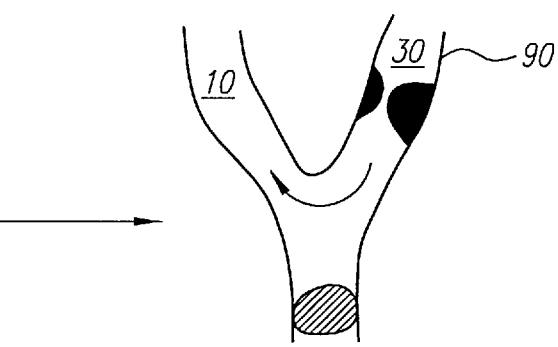
FIG. 7D depicts flow reversal from the ICA toward the ECA which occurs due to increased collateral flow.
Figure 7E:
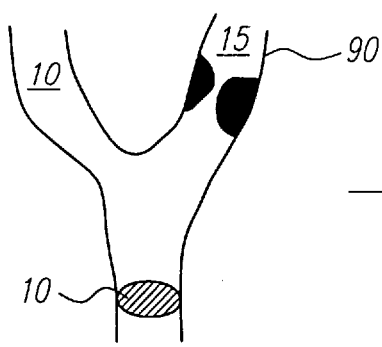
FIG. 7E depicts absence of flow reversal from the ICA toward the ECA.
Figure 7F:
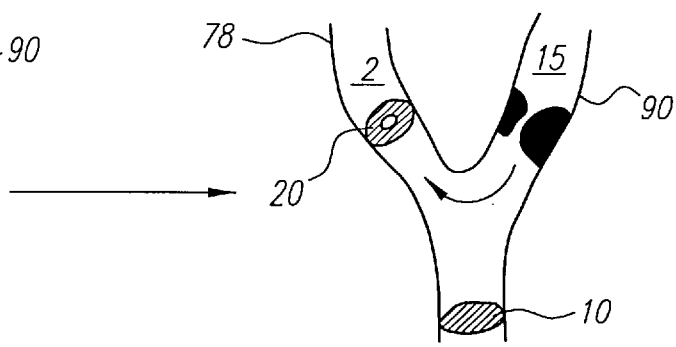
FIG. 7F depicts flow reversal from the ICA toward the ECA after partial occlusion of the ECA.

FIGS. 7A, 7B, 7C, 7D, 7E, and 7F depict changes of the blood pressure in CCA 80, ECA 78, and ICA 90 in response to having a flow limiting lesion in the ICA and an occluder in the CCA. In FIG. 7A, which depicts normal carotid circulation, CCA 80 generally has a blood pressure of approximately 120 mmHg. Antegrade blood flow occurs from the CCA to ICA 90, which generally has a pressure of approximately 70 mmHg, and to ECA 78, which generally has a pressure of approximately 40 mmHg. When ICA 90 has atheromatous lesion 70 as depicted in FIG. 7B, the pressure in ICA 90 is reduced to approximately 40. When occluder 10 is expanded to occlude CCA 80 as depicted in FIG. 7C, the pressure in the CCA is reduced to approximately 0 mmHg, and the pressure in ECA 78 and ICA 90 distal to atheromatous lesion 70 is reduced to approximately 10 mmHg from collateral flow. As flow further increases from the contralateral hemisphere across the circle of Willis, the pressure distal to the atheromatous lesion in the ICA will generally be increased to approximately 30 mmHg, causing flow reversal from the ICA and up to the ECA as depicted in FIG. 7D. However, when flow does not significantly increase from the contralateral hemisphere, the pressure in ICA 90 distal to the atheromatous lesion will generally be approximately 15, which is insufficient to generate the pressure gradient between the ICA and the ECA to reverse blood flow, as depicted in FIG. 7E. In this case, constrictor 20 is expanded in ECA 78 as depicted in FIG. 7F, causing reduction of the pressure in the ECA distal to the constrictor to approximately 2 mmHg. This reduction in the ECA pressure creates a sufficient gradient between the ICA and the ECA to reverse flow down the ICA and up into the ECA.

Figure 8A:
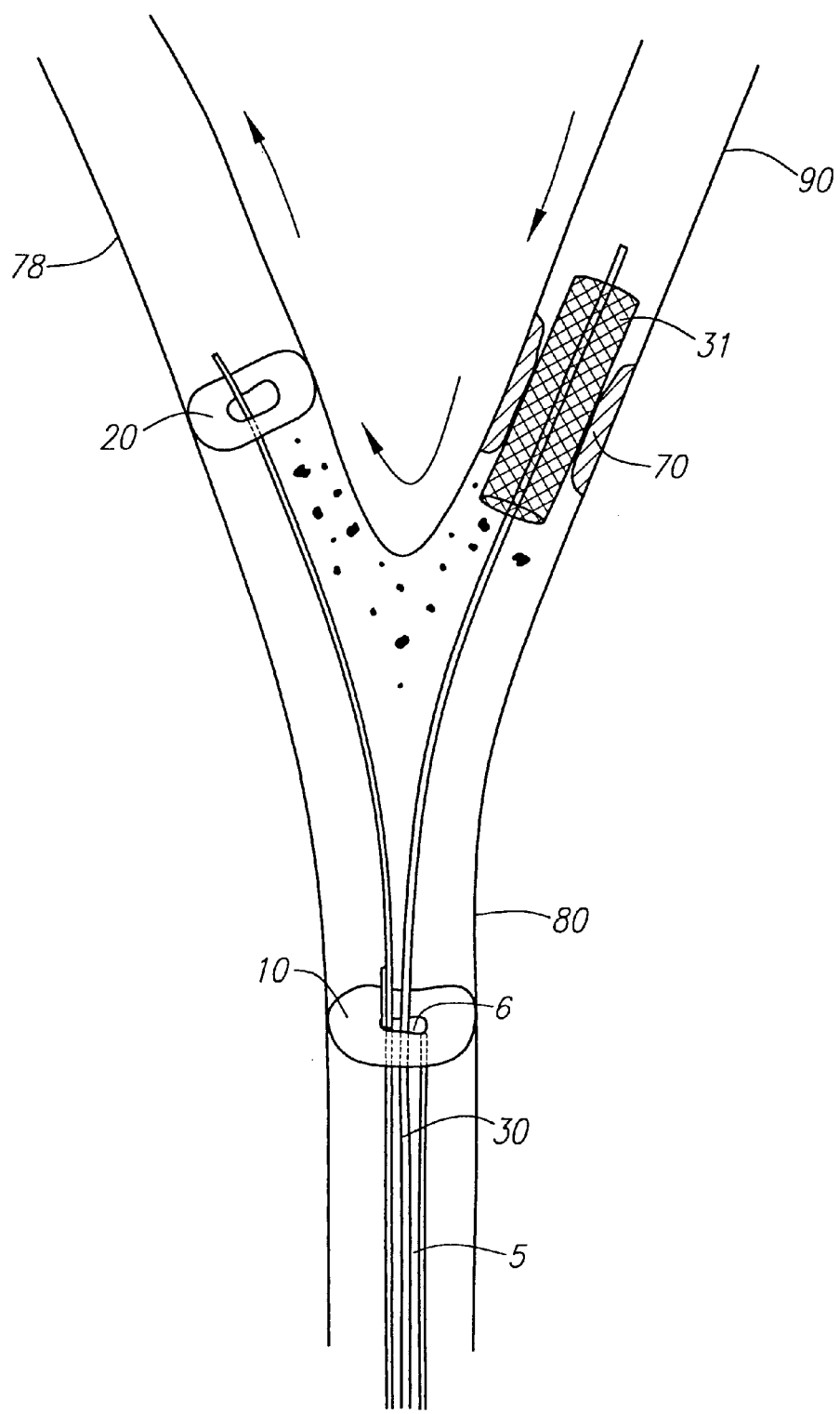
FIG. 8A depicts a stent introduced through the device of FIG. 6B and deployed in the ICA.

After blood reversal is established from the ICA to the ECA, the devices and methods described above can be used in any carotid procedures. For example, in FIG. 8A, catheter 30 carrying stent 31 is introduced through lumen 5 and port 6. The stent is shown deployed over atheromatous lesion 70 in ICA 90, thereby compressing the lesion and enlarging the lumenal diameter. Compression of the atheroma by the stent often generates embolic debris, including calcium, atheromatous plaque, and thrombi. With reversal of blood flow from the ICA to the ECA, distal embolization to the intracranial cerebral arteries is avoided, thereby minimizing risk of ischemic stroke. Distal embolization of the branches of the ECA has far less devastating consequences than the ICA. The ECA is sometimes ligated to control hemorrhage from a branch that is clinically inaccessible. Blood flow through the affected ECA and its branches is reduced but not abolished due to retrograde contralateral collateral circulation.

Figure 8B:
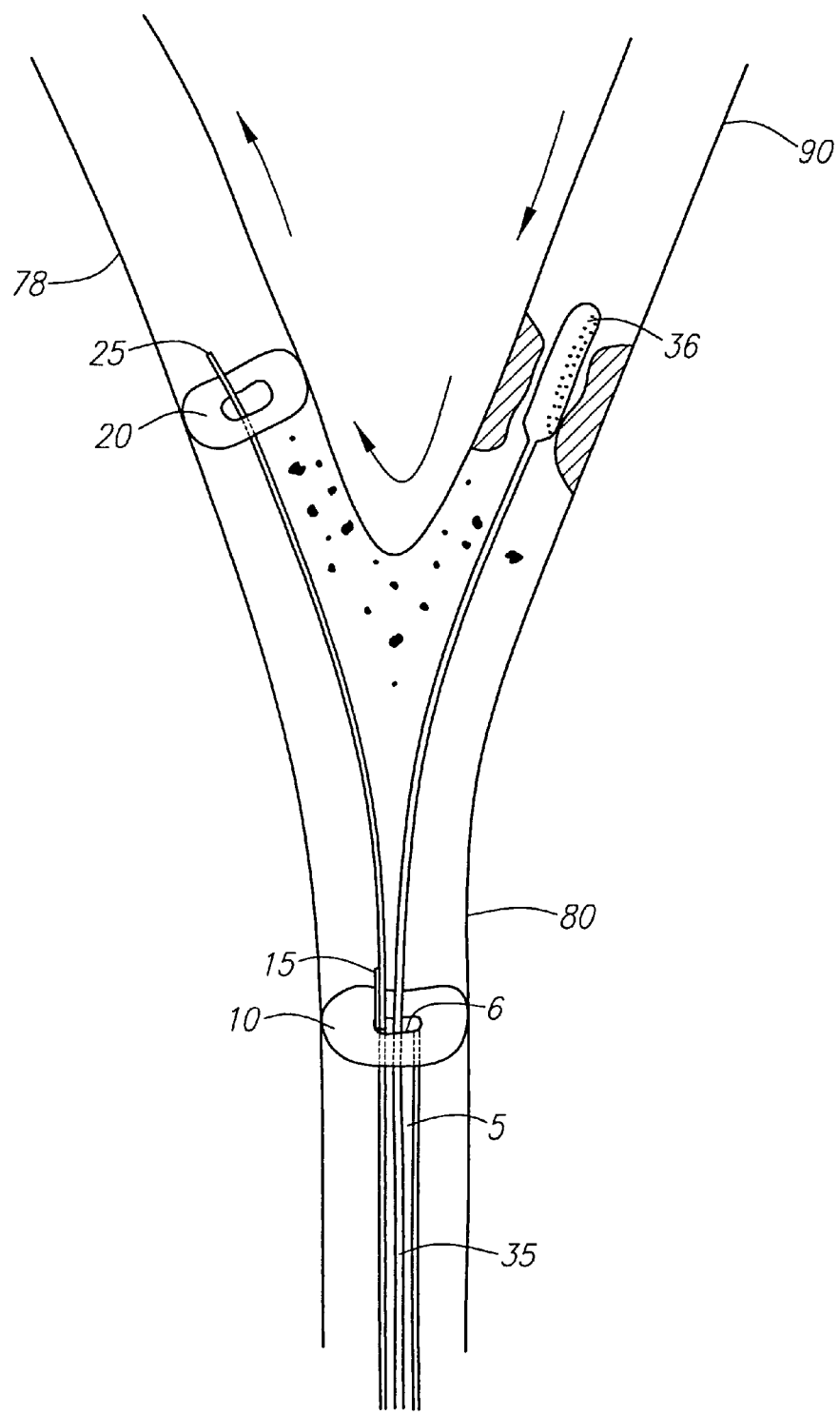
FIG. 8B depicts an atherectomy catheter introduced through the device of FIG. 6 in the ICA.

In FIG. 8B, atherectomy catheter 35 is introduced through lumen 5 and port 6. After blood reversal is established from the ICA to the ECA, atherectomy device 36 is positioned over atheromatous lesion 70 and operated to remove the occluding lesion. Embolic debris generated during the procedure is diverted from ICA 90 toward ECA 78, thereby preventing distal embolization and ischemic stroke. The construction of atherectomy catheters is well known in the art and will not be repeated in detail here. The reader is referred instead to Fischell, U.S. Pat. No. 5,409,454, Fischell, U.S. Pat. No. 4,898,575, Rydell, U.S. Pat. No. 4,857,045, Yock, U.S. Pat. Nos. 4,794,931, 5,000,185, and 5,313,949, Jang et al., U.S. Pat. No. 5,507,292, Farr, U.S. Pat. Nos. 4,950,277, 4,986,807, 5,019,088, Shiber, U.S. Pat. Nos. 4,894,051, 4,957,482, 4,979,939, 5,007,896, 5,024,651, 5,135,531, Summers, U.S. Pat. No. 5,087,265, Plassche et al., U.S. Pat. No. 5,318,576, Belknap, U.S. Pat. No. 5,366,464, Jang et al., U.S. Pat. No. 5,402,790, Mazur et al., Catherization and Cardiovascular Diagnosis 31:79–84 (1994), Fischell et al., U.S. Pat. Nos. 4,886,061, 5,100,425, and Barbut et al., U.S. Pat. No. 5,662,671, all of which are incorporated herein by reference as if fully set forth herein. In other embodiments, catheter 35 may carry angioplasty balloon 36.

Figure 9:
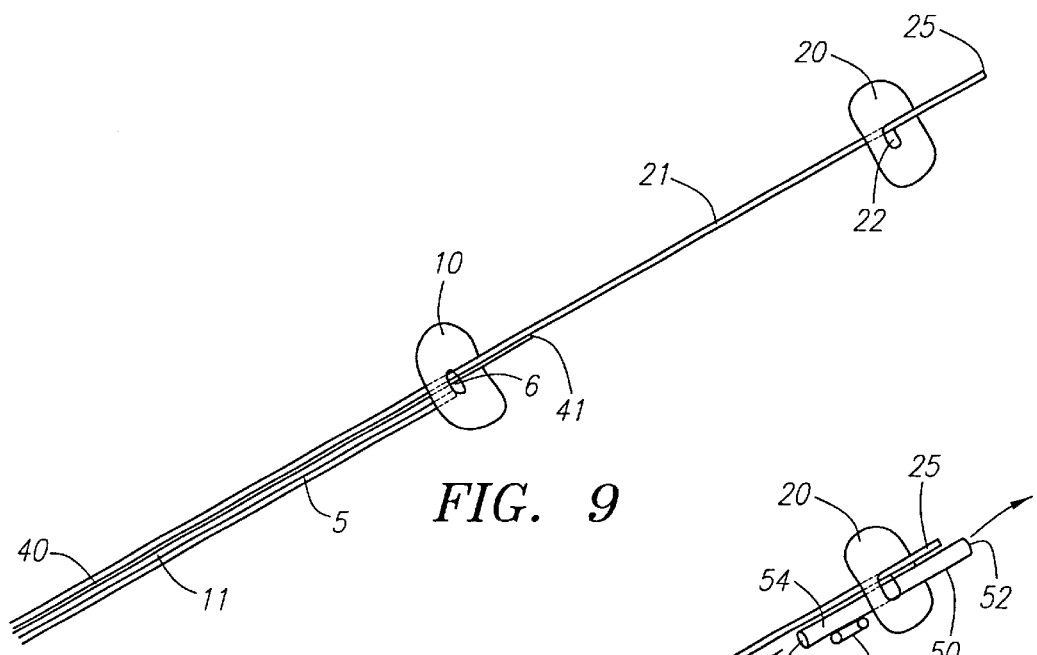
FIG. 9 depicts another embodiment of the device having a second lumen.

FIG. 9 depicts another embodiment of the device having second lumen 40 communicating with second port 41. The second lumen and port are adapted for delivering a pharmaceutical agent, e.g., tissue plasminogen activator (t-PA), a neuroprotective agent, or an angiographic dye. Local administration of a thrombolytic agent to an occluded carotid artery reduces the risk associated with systemic thrombolytic therapy, i.e., hemorrhage. Administration of dye through port 41 provides fluoroscopic verification of flow reversal in the carotid arteries.

Figure 10:
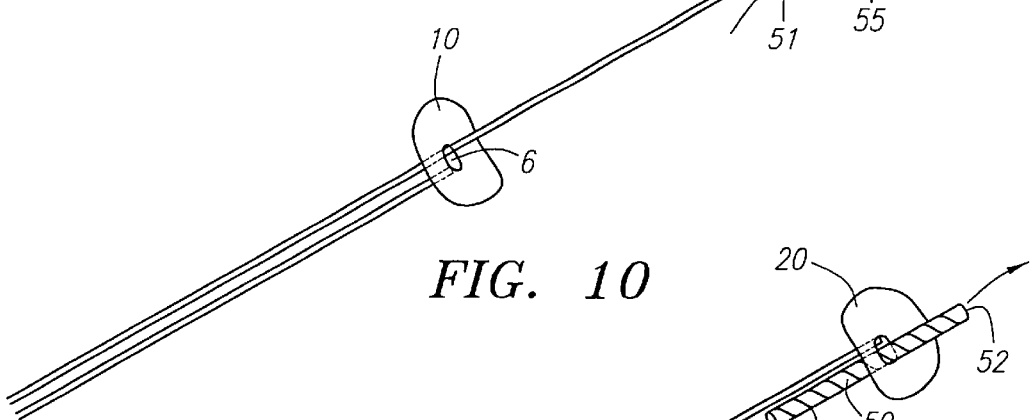
FIG. 10 depicts another embodiment of the device having a shunt and a pump.

A pump may be incorporated in the devices to facilitate reversal of blood flow from the ICA toward the ECA. One embodiment of the devices carrying pump 55 is shown in FIG. 10. The pump is operably associated with shunt 50, which comprises an elongate tube having lumen 54 communicating with proximal end 51 and distal end 52. The shunt is mounted through second occluder 20. In use, the device is inserted over a guide wire in the carotid arteries, so that first occluder 10 is positioned in the CCA, distal end 52 of the shunt is positioned in the ECA, and proximal end 51 is position in the CCA, close to the ICA bifurcation. Preferably, first occluder 10 is expanded to occlude the CCA. If flow reversal down the ICA and into the ECA fails to occur, second occluder 20 is expanded to further reduce the pressure in the ECA. Alternatively, the second occluder is expanded to constrict the ECA, followed by expansion of the first occluder to partially or completely occlude the CCA. When flow reversal into the ECA is undetected or insufficient, pump 55 is activated to pass blood from proximal end 51 in the CCA/bifurcation, through lumen 54, and exit distal end 52 in the ECA. The flow rate can be adjusted to the minimum rate required to maintain flow reversal in the ICA. The pump is heparin coated to minimize thrombi formation.

Figure 11A:
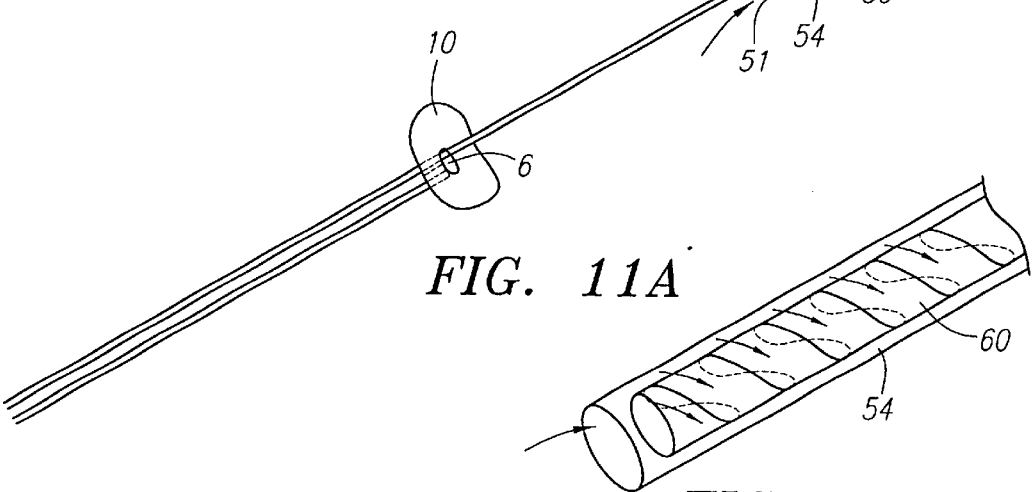
FIG. 11A depicts another embodiment of the device having a shunt and a helical screw pump.
Figure 11B:
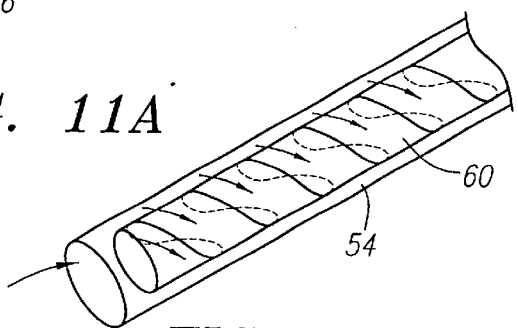
FIG. 11B depicts the helical screw pump of FIG. 11A included in the lumen of the shunt.

Another embodiment of the pump is shown in FIGS. 11A and 11B. Shunt 50, having an elongate tube having lumen 54 communicating with proximal end 51 and distal end 52, is mounted through second occluder 20. Heparin coated helical screw pump 60 is included in lumen 54 of the shunt as depicted in FIG. 11B. In use, first occluder 10 is positioned in the CCA, distal end 52 of the shunt is positioned in the ECA, and proximal end 51 is position in the CCA, close to the ICA bifurcation. Preferably, the first occluder is expanded to occlude the CCA, followed by expansion of the second occluder to constrict the ECA. When flow reversal toward the ECA is undetected or insufficient, pump 60 is activated and rotates clockwise to pass blood from proximal end 51 in the CCA/bifurcation, through lumen 54, and exit distal end 52 in the ECA. Blood is moved within lumen 54 of the shunt between threads of the helical screw pump. The flow rate can be adjusted to the minimum rate required to maintain flow reversal in the ICA. This reversal can typically be accomplished by rotation of the screw pump at 100 rpm, 200 rpm, 300 rpm, 400 rpm, 500 rpm or higher.

Figure 12A:
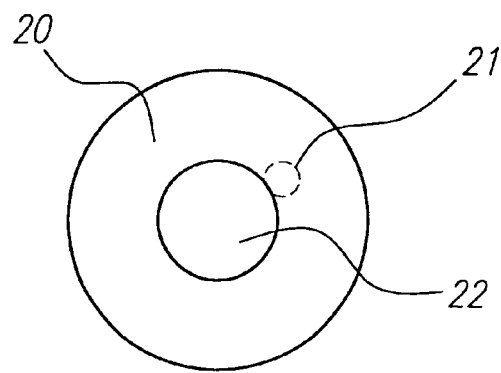
FIG. 12A depicts a cross-sectional view of the constrictor having a central opening for passage of blood.
Figure 12B:
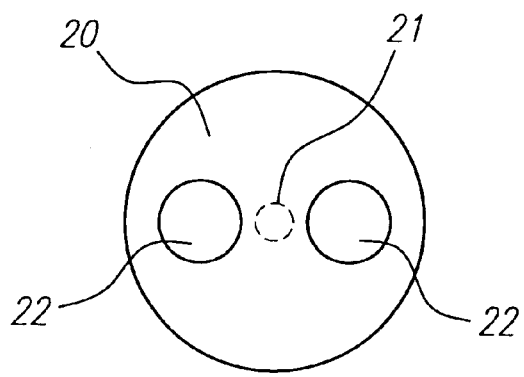
FIG. 12B depicts a cross-sectional view of the constrictor having two opening for passage of blood.
Figure 12C:
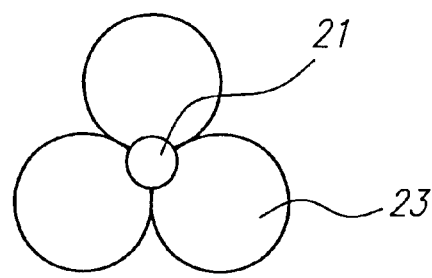
FIG. 12C depicts a cross-sectional view of the constrictor comprising three expandable balloons.

FIGS. 12A, 12B, and 12C depict cross-sectional views of different constructions of the constrictor for allowing blood flow past the constrictor. In FIG. 12A, constrictor 20 is a toroidal balloon which communicates with inflation lumen 21 and includes central opening 22 for passage of blood. In FIG. 12B, balloon constrictor 20 communicates with inflation lumen 21 and communicates with two openings 22 for passage of blood. In FIG. 12C, the constrictor comprises three expandable balloons 23 communicating with inflation lumen 21. When inserted in the ECA, blood passes in the gap between the arterial wall and the expanded balloons. In all three of these designs the constrictor, when expanded, maintains contact with the arterial wall, thus reducing trauma and further emboli dislodgement caused by the balloon impacting the vessel wall by oscillating in the blood flow.

Figure 13:
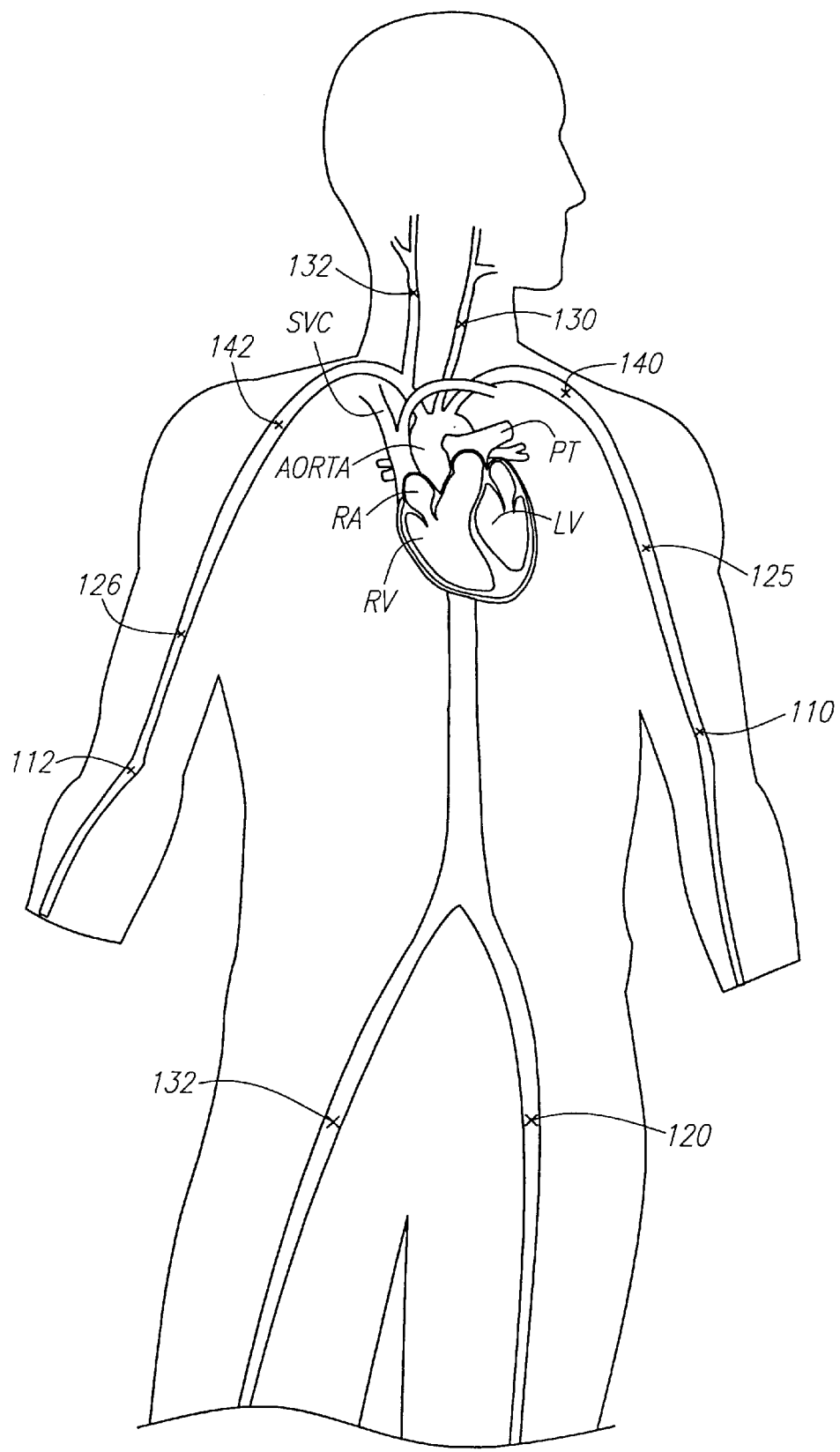
FIG. 13 depicts incision sites on various peripheral arteries for the insertion of the medical device.

FIG. 13 depicts different sites of entry for the devices disclosed herein. An incision can be made on a peripheral artery, such as right femoral artery 122, left femoral artery 120, right brachial artery 112, left brachial artery 110, right axillary artery 126, left axillary artery 115, right subclavian artery 142, or left subdlavian artery 140. An incision can also be made on right carotid artery 132 or left carotid artery 130 in emergency situations.

The length of catheter will generally be between 10 and 200 centimeters, preferably approximately between 30 and 150 centimeters. The inner diameter of the catheter lumen will generally be between 0.2 and 0.8 centimeters, preferably approximately between 0.3 and 0.5 centimeters. The diameter of the expanded occluder will generally be between 0.3 and 2 centimeters, preferably approximately 0.5 and 1.0 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for flow reversal, comprising the steps of:
   inserting a catheter into a carotid artery, the catheter having a proximal end, a distal end, and an expandable device on the distal end;
   locating the expandable device within a common carotid artery proximal a lesion;
   expanding the device to at least partially obstruct the common carotid artery; and
   performing an interventional procedure on the lesion while blood flow in an internal carotid artery is reversed to pass toward and into an external carotid artery.

2. The method of claim 1, wherein the catheter further comprises a second expandable device, and wherein the method further comprises the steps of:
   locating the second expandable device within the external carotid artery; and
   expanding the second expandable device to at least partially obstruct the external carotid artery.

3. The method of claim 1, wherein the internal carotid artery has an atheromatous lesion.

4. The method of claim 1, further comprising the step of treating an atheromatous lesion in the internal carotid artery by advancing a second catheter distal to the expanded device in the common carotid artery and into a region adjacent the lesion.

5. The method of claim 1, wherein the expandable device is a balloon.

6. The method of claim 1, wherein the expandable device is a toroidal balloon.

7. The method of claim 1, wherein the catheter has a lumen that communicates with a port distal the expandable device.

8. The method of claim 7, further comprising the step of:
   advancing a therapeutic instrument through the lumen and port distal the expandable device; and
   contacting the therapeutic instrument with the lesion.

9. The method of claim 8, wherein the therapeutic instrument is an angioplasty catheter.

10. The method of claim 8, wherein the therapeutic instrument is a stent.

11. The method of claim 1, further comprising the step of occluding the external carotid artery with a second expandable device and activating a pump traversing the second expandable device.

* * * * *